(12) United States Patent
Wimpenny et al.

(10) Patent No.: US 12,427,259 B2
(45) Date of Patent: Sep. 30, 2025

(54) CARTRIDGE ASSEMBLY FOR A DRUG DELIVERY DEVICE AND METHOD FOR ASSEMBLING THE SAME

(71) Applicant: Sanofi, Paris (FR)

(72) Inventors: Steven Wimpenny, Warwick (GB); David Aubrey Plumptre, Warwick (GB); Robert Veasey, Warwick (GB); Ian McFaul, Warwick (GB); Hugh Smith, Warwick (GB); Paul Griffin, Warwick (GB)

(73) Assignee: Sanofi, Paris (FR)

( * ) Notice: Subject to any disclaimer, the term of this patent is extended or adjusted under 35 U.S.C. 154(b) by 1057 days.

(21) Appl. No.: 17/260,407

(22) PCT Filed: Jul. 15, 2019

(86) PCT No.: PCT/EP2019/068966
§ 371 (c)(1),
(2) Date: Jan. 14, 2021

(87) PCT Pub. No.: WO2020/016158
PCT Pub. Date: Jan. 23, 2020

(65) Prior Publication Data
US 2021/0260291 A1 Aug. 26, 2021

(30) Foreign Application Priority Data
Jul. 18, 2018 (EP) .................... 18305974

(51) Int. Cl.
*A61M 5/24* (2006.01)
(52) U.S. Cl.
CPC ....... *A61M 5/24* (2013.01); *A61M 2005/2444* (2013.01); *A61M 2005/2492* (2013.01)

(58) Field of Classification Search
CPC ........... A61M 5/24; A61M 2005/2444; A61M 2005/2492; A61M 2005/244;
(Continued)

(56) References Cited

U.S. PATENT DOCUMENTS 6,648,859 B2 * 11/2003 Bitdinger ............... A61M 5/24
604/218
8,574,199 B2 * 11/2013 von Bulow ....... A61M 5/31585
604/110
(Continued)

FOREIGN PATENT DOCUMENTS

| CN | 1468118 | 1/2004 |
|---|---|---|
| CN | 102917740 | 2/2013 |

(Continued)

OTHER PUBLICATIONS

PCT International Preliminary Report on Patentability in International Application No. PCT/EP2019/068966, dated Jan. 19, 2021, 7 pages.
(Continued)

*Primary Examiner* — Laura A Bouchelle
(74) *Attorney, Agent, or Firm* — Bond, Schoeneck & King, PLLC

(57) ABSTRACT

A cartridge assembly for a drug delivery device can include: a cartridge holder, a cartridge containing a drug, and a fixing member, wherein the cartridge holder includes an interior cartridge holding section, the cartridge being arranged in the cartridge holding section, wherein the fixing member is axially secured to the cartridge holder and secures the cartridge permanently in the cartridge holder.

20 Claims, 4 Drawing Sheets

(58) Field of Classification Search
CPC .. A61M 2005/3142; A61M 2005/2403; A61M 2005/2407; A61M 2005/2411; A61M 2005/2414; A61M 2005/2433; A61M 2005/2437

See application file for complete search history.

(56) References Cited

U.S. PATENT DOCUMENTS

| | | | | |
|---|---|---|---|---|
| 2004/0215152 | A1* | 10/2004 | Kirchhofer | A61M 5/31553 604/211 |
| 2010/0137809 | A1* | 6/2010 | Tschirren | A61M 5/24 604/187 |
| 2011/0172602 | A1 | 7/2011 | Eaton | |
| 2012/0101439 | A9 | 4/2012 | Slate et al. | |
| 2013/0211326 | A1 | 8/2013 | Dasbach et al. | |
| 2013/0226082 | A1* | 8/2013 | Klintenstedt | A61M 5/00 604/93.01 |
| 2013/0253432 | A1 | 9/2013 | Avery et al. | |
| 2013/0253433 | A1 | 9/2013 | Senior et al. | |
| 2014/0358084 | A1 | 12/2014 | McLoughlin et al. | |
| 2015/0011949 | A1 | 1/2015 | Soerensen | |
| 2016/0022914 | A1 | 1/2016 | Mounce et al. | |
| 2017/0196770 | A1 | 7/2017 | Klintenstedt et al. | |
| 2018/0071458 | A1 | 3/2018 | Oestergaard | |

FOREIGN PATENT DOCUMENTS

| | | |
|---|---|---|
| CN | 102958550 | 3/2013 |
| CN | 103167888 | 6/2013 |
| CN | 104136059 | 11/2014 |
| CN | 104582760 | 4/2015 |
| CN | 108136130 | 6/2018 |
| EP | 1423079 | 7/2006 |
| EP | 2043708 | 12/2010 |
| JP | 2013-535282 | 9/2013 |
| JP | 2013-542807 | 11/2013 |
| WO | WO 2002/030495 | 4/2002 |
| WO | WO 2011/032883 | 3/2011 |
| WO | WO 2011/124632 | 10/2011 |
| WO | WO 2011/131778 | 10/2011 |
| WO | WO 2011/131779 | 10/2011 |
| WO | WO 2012/017063 | 2/2012 |
| WO | WO 2012/064258 | 5/2012 |
| WO | WO 2012/064259 | 5/2012 |
| WO | WO 2012/130704 | 10/2012 |
| WO | WO 2013/110769 | 8/2013 |
| WO | WO 2013/124118 | 8/2013 |
| WO | WO 2016/065220 | 4/2016 |
| WO | WO 2016/091554 | 6/2016 |
| WO | WO 2016/150900 | 9/2016 |
| WO | WO 2017/072233 | 5/2017 |
| WO | WO 2017/186435 | 11/2017 |
| WO | WO 2018/109689 | 6/2018 |

OTHER PUBLICATIONS

PCT International Search Report and Written Opinion in International Application No. PCT/EP2019/068966, dated Aug. 14, 2019, 11 pages.

Third Party Observations in European Appln. No. 19737769.0, dated Jun. 19, 2023, 18 pages.

* cited by examiner

CARTRIDGE ASSEMBLY FOR A DRUG DELIVERY DEVICE AND METHOD FOR ASSEMBLING THE SAME

CROSS-REFERENCE TO RELATED APPLICATIONS

The present application is the national stage entry of International Patent Application No. PCT/EP2019/068966, filed on Jul. 15, 2019, and claims priority to Application No. EP 18305974.0, filed on Jul. 18, 2018, the disclosures of which are incorporated herein by reference.

TECHNICAL FIELD

The present disclosure relates to a cartridge assembly, particularly a cartridge assembly for a drug delivery device, preferably an injection device and/or a pen-type device, such as a pen-type injector. Furthermore, the present disclosure relates to a set of cartridge assemblies, a kit for assembling a cartridge assembly, and a method for manufacturing a cartridge assembly. Moreover, the present disclosure relates to a drug delivery device comprising the cartridge assembly.

BACKGROUND

In some drug delivery devices, where a single drive mechanism which may be housed in a housing of the drug delivery device is used in conjunction with several cartridges or ampules to dispense drug contained in the cartridge or ampule from the device, usually a cartridge holder of the device is releasably connected to the housing and can be removed from the housing to replace a used cartridge. For doing so, the cartridge holder is disconnected from the housing, the used cartridge is removed from the holder and replaced with a new cartridge which is inserted into the cartridge holder, where the cartridge holder is again attached to the housing and the device is ready to be used again to dispense drug from the new cartridge.

Devices of this kind, however, do have several risks. For example, a cartridge containing a drug for which the mechanism of the drug delivery device is not specifically designed, i.e. a wrong drug, can be inserted into the cartridge holder and the user does not realize that he has put the wrong drug cartridge into the cartridge holder. This mistake may be lethal for the user and is also likely to occur as cartridges with different drugs usually look similar.

Furthermore, the cartridge, if sold as a separate item, is usually easily damaged, in particular as the standard cartridges are usually glass cartridges. Still further, in a specific cartridge holder, usually only a cartridge of one specific dimension can be retained and connected to a drive mechanism. Accordingly, cartridges of various dimensions such as of different length and/or diameter can usually not be connected to the same drive mechanism easily.

SUMMARY

The present disclosure describes an improved cartridge assembly for a drug delivery device, a method for assembling the cartridge assembly and/or further improvements or configurations associated with the cartridge assembly. These features and potentially other features are solved by the present disclosure and, particularly, by the subject-matter of the independent claims. Advantageous embodiments and refinements are subject to the dependent claims.

One aspect of the present disclosure relates to a cartridge assembly, in particular one for a drug delivery device, such as a pen-type device and/or an injection device. Another aspect relates to the drug delivery device. The drug delivery device expediently comprises the cartridge assembly as described herein and a housing. The cartridge assembly may be releasably secured to the housing. Within the housing, a drive mechanism, which is preferably designed to drive a dispensing action in order dispense drug or medicament from the cartridge, may be retained or at least one or more elements thereof, such as a piston rod.

The cartridge assembly comprises a cartridge holder, a cartridge containing a drug or a medicament and a fixing member. The cartridge holder comprises or defines an interior cartridge holding section. The interior cartridge holding section may be delimited laterally and/or circumferentially by a sidewall of the cartridge holder. The cartridge is arranged in the cartridge holding section. The fixing member secures the cartridge, preferably permanently, in the cartridge holder. The fixing member may abut or mechanically cooperate with the cartridge to secure the cartridge in the cartridge holder. The cartridge may be a glass cartridge. The cartridge may have a main body portion and a head portion which are connected via a neck portion, which may have a reduced diameter as compared to the main body portion and/or the neck portion. The main body portion may be cylindrical. In the head portion, a dispensing opening of the cartridge may be arranged. The dispensing opening may be closed by a pierceable septum, which can be pierced by a needle to provide fluid communication between the interior of the cartridge and the exterior.

The fixing member is secured to the cartridge holder, preferably permanently and/or irreleasably. For example, the fixing member is axially and/or rotationally secured to the cartridge holder. In particular, relative axial movement between the cartridge holder and the fixing member may be prevented in at least one axial direction or two opposite axial directions. Relative rotational movement may be prevented in one rotational direction or in two opposite rotational directions.

The cartridge holder may have an opening which delimits the cartridge holder in the proximal direction. Thus, the opening may be provided at a proximal end of the cartridge holder. The opening may be designed to receive the cartridge such that the cartridge may be guided into the cartridge holder via the opening. The fixing member may be connected to the cartridge holder in the region of the proximal opening. When it is secured to the cartridge holder, movement of the fixing member in the proximal direction away from the cartridge holder may be prevented. In the distal direction, the cartridge holder may be delimited by a distal end face. A needle connector may be provided at the distal end of the cartridge holder. A distal end face of the cartridge may be arranged to abut an interior proximal face of the cartridge holder. In other words, in the distal direction, the cartridge may not be moved relative to the cartridge holder. The cartridge may be secured permanently in the cartridge holder by the fixing member. Preferably, without the fixing member, the cartridge could be removed from the cartridge holder.

As the cartridge is expediently permanently secured in the cartridge holder, the cartridge assembly may form one unit or a single unit of consumable material. That is to say, the cartridge assembly in its entirety may be a disposable item, which is disposed after the drug or medicament in the cartridge has been dispensed.

If the cartridge is permanently secured in the cartridge holder by the fixing member several advantages are attained. For example, the cartridge is always protected by the cartridge holder when the user handles the cartridge assembly. The risk of a cartridge breaking is then considerably reduced as opposed to systems where the cartridge in the holder needs to be replaced by the user. Rather, in the proposed system, the entire cartridge assembly is replaced with a new one.

Moreover, as the cartridge assembly comprises not only the cartridge but also other elements like the cartridge holder and the fixing member, it is easier to dedicate or code the cartridge to a particular drive mechanism or housing for a drug delivery device, in particular without having to change the design of the cartridge. Thus, a standard cartridge can be used. Moreover, the dedication or coding may be provided by means of the fixing member. Thus, cartridge assemblies with the same drug or medicament and/or of the same filling levels of the cartridge may have fixing members of identical configurations. Cartridge assemblies with the different drug or medicaments and/or different filling levels of the cartridge may have fixing members of different configurations. Thus the fixing member may be used to distinguish a particular cartridge assembly from other cartridge assemblies. Fixing members of different colors may be used to provide information about the content of the cartridge to the user.

By means of dedication or coding it can be assured that the cartridge assembly can only be or will only be used together with a matching drive mechanism, i.e. a mechanism which has been specifically designed for delivering the content contained in the cartridge. For example, the cartridge assembly may be mechanically coded to the drive mechanism or to the housing which houses the drive mechanism and to which the cartridge assembly should be connected to form a drug delivery device. One or more coding features may be provided on the cartridge assembly which are configured to interact with one or more corresponding coding features on the housing or the drive mechanism to prevent connection of the cartridge assembly to the housing unless the coding features match. The coding features may be realized by interface features which are disclosed further below.

Still further, by means of different fixing members, cartridges of different dimensions may be secured in cartridge holders which have the same configurations. The dimensional adjustment may be achieved by the fixing member.

In an embodiment, the fixing member prevents the cartridge from being removed from the cartridge holder, in particular via the proximal opening of the cartridge holder. Preferably, the fixing member is designed so as to secure the cartridge within the cartridge holder unless the fixing member is damaged. A damaged fixing member may indicate to a user that the cartridge assembly has been tampered with and the user may discard the entire assembly as it is unsure, whether the correct drug or medicament is contained in the assembly.

In an embodiment, the fixing member has a main body. The main body may have a ring-like or sleeve-like shape. The main body may extend around the cartridge, when assembled to the cartridge holder. The main body may extend around the circumference of the cartridge, preferably the entire circumference. The cartridge may be arranged within or extend through the main body. If the main body is closed in the angular direction, i.e. without an open angular end face, as is the case for a ring or sleeve-shaped main body, for example, the main body is more stable against deformation, particular in the radial direction. This may strengthen the connection between the fixing member and the cartridge holder and may help to ensure that the cartridge assembly cannot be disassembled.

In an embodiment, the fixing member has one or more securing features. The respective securing feature, for example a snap feature, may be designed to secure the fixing member axially with respect to the cartridge holder, preferably in one axial direction or in both axial directions. The fixing member may have one or more securing fingers. The respective securing finger may be provided with a securing feature. The respective securing finger may be flexible. That is to say, it may be deflected, particularly in an elastic way and/or in the radial direction. Thus, the respective securing feature may be resiliently connected to the main body via the associated securing finger. By means of the securing finger(s), the fixing member may be reliably secured to the cartridge holder. Consequently, the fixing member enables a cartridge assembly, which can, once assembled, not be disassembled easily, for example without destructing one of the associated components.

In an embodiment, the securing fingers extend in an axial direction, e.g. away from the main body. The axial direction may be the distal direction. The securing feature may protrude radially, in particular radially outwardly, from the respective securing finger.

The terms "distal" and "proximal" as used herein may refer to opposite axial directions or ends. "Distal" may refer to a direction towards the dispensing end or an end of a component of a drug delivery device which is or is to be arranged closest to the dispensing end of the cartridge, the cartridge assembly or the drug delivery device. "Proximal" may refer to a direction away from the dispensing end or an end which is or is to be arranged further away from the dispensing end of the cartridge, the cartridge assembly or the drug delivery device. The terms "axial", "radial", or "angular" as used herein may be used with respect to a main longitudinal axis of the device or the cartridge assembly or components thereof, e.g. the axis which extends through the proximal and distal ends of the cartridge assembly or the drug delivery device.

In an embodiment, the opening of the cartridge holder may provide access for the cartridge to the interior cartridge holding section of the cartridge holder. At a distal end of the cartridge holder a needle mounting feature or needle connector may be provided, for example a thread. A distal section of the cartridge holder may have a reduced inner and/or outer diameter as compared to the proximal section of the cartridge holder. The respective section of the cartridge holder may be adjusted to the portion of the cartridge arranged in that section. The head portion of the cartridge may be arranged in the distal section and the main body portion may be arranged in the proximal section.

In an embodiment, at least a section of the fixing member is arranged between the cartridge and an inner wall of the cartridge holder. Particularly, that section of the fixing member which is provided with the securing feature, e.g. the securing finger, may be arranged between an inner wall of the cartridge holder and the cartridge. In this way, the cartridge may prevent or counteract a radial movement, e.g. an inward movement, which would be required to disengage the securing feature from the cartridge holder, once the cartridge assembly has been assembled. Thus, disassembling of the cartridge assembly may be made even more difficult.

In an embodiment, the fixing member comprises one or a plurality of fixing features, which are arranged to retain the cartridge in the cartridge assembly. The respective fixing feature is expediently arranged to mechanically cooperate with the cartridge. The respective fixing feature may be axially offset from the securing feature(s). The fixing feature(s) may be arranged more proximally than the securing feature(s). The fixing feature(s) and the securing feature(s) may be arranged on opposite sides of the main body. The fixing feature(s) may extend in a radial direction. The direction may be opposite to the one into which the securing feature(s) extends. The fixing feature(s) may extend in the radial inward direction. A distal surface of the fixing feature(s) may be arranged to contact or contacts a proximal surface of the cartridge, e.g. a proximal end surface such as a proximal rim or edge of the cartridge. By means of the fixing feature(s), the cartridge may be reliably retained within the cartridge holder. Without the fixing feature(s), the cartridge may be removed from the cartridge holder.

In an embodiment, the fixing member comprises one or a plurality of fixing fingers. The respective fixing finger may be provided with a fixing feature. The fixing fingers may extend in an axial direction away from the main body. The axial direction may be the proximal direction. The fixing finger(s) and the securing finger(s) may be aligned angularly, i.e. they may be provided at corresponding angular positions relative to the main body. The fixing feature may extend radially relative to or protrude radially from the associated fixing finger, preferably inwardly.

In an embodiment, the fixing finger(s) is (are) less flexible than the securing finger(s). The fixing finger(s) may be more rigid or stiffer than the securing finger(s). Accordingly, the fixing finger(s) may be harder to deflect, in particular in the radial direction, than the securing finger(s). In this way, it can be guaranteed that the force for securing the fixing member to the cartridge holder, which might require a radial (inward) movement of the fixing feature(s), is less than the force required to deflect the fixing finger(s) in the radial (outward) direction, which would be required to remove the cartridge from the cartridge assembly.

If the fixing fingers are flexible, the fixing member can be fixed to the cartridge holder before the cartridge is introduced into the cartridge holder, particularly via the proximal opening. For inserting the cartridge into the cartridge holder, the fixing fingers may be deflected in the radial direction to increase the diameter of an opening defined between the fixing features until the cartridge can be guided through that opening. Once the cartridge has passed the fixing features the fixing fingers may be moved back, e.g. to a non-deflected position, preferably on account of their own resiliency. Then the diameter of the opening may be less than the diameter of the cartridge, e.g. of the main body portion, and the fixing features may secure the cartridge in the holder. Of course, this may also be achieved by means of just one fixing finger.

If the fixing finger(s) is (are) rigid, the cartridge may be introduced into the cartridge holder before the fixing member is fixed to the cartridge holder. During fixing of the fixing member to the cartridge holder, the securing finger(s) may be guided in a region between an outer wall of the cartridge and an inner wall of the cartridge holder until the securing features engage corresponding features on the cartridge holder, e.g. corresponding snap features like snap pockets. If the fixing finger(s) cannot be radially deformed or deflected without being broken, the cartridge cannot be removed from the cartridge assembly without damaging at least one fixing finger. This will indicate that the cartridge assembly has been tampered with.

In an embodiment, a bung closes the interior of the cartridge, in particular at the proximal end. The bung may be movably retained in the cartridge. The proximal opening of the cartridge may be sealed by the bung. Accordingly, a proximal opening of the cartridge may be closed by a movable bung which can be displaced in the distal direction relative to the cartridge in order to dispense drug or medicament, such as liquid drug or medicament, from the cartridge. The bung is expediently arranged in the main body portion of the cartridge. The bung may be part of the cartridge assembly. The fixing feature(s) may be arranged proximally offset from a proximal end of the bung.

In an embodiment, a section of the fixing member and/or a section of the cartridge protrudes from the cartridge holder, particularly proximally. The section which protrudes from the cartridge holder may be a section of the main body, preferably only a section of the main body, and/or a section of the fixing finger(s), preferably only a section thereof or the entire fixing finger. The section of the cartridge which protrudes proximally from the cartridge holder may be the section where the bung is arranged or a section which is arranged further away from the dispensing end of the cartridge than the bung. Nevertheless, as the section of a cartridge which may protrude proximally from the cartridge holder is more prone to damages, the majority of the cartridge is expediently arranged within the cartridge holder e.g. in the cartridge holding section. For example of the total length of the cartridge more than 50%, 60%, 70%, 80% and/or 90% is arranged within the cartridge holding section and/or in the cartridge holder. Consequently, the remaining part of the cartridge may protrude from a proximal opening of the cartridge holder.

In the section of the fixing member which protrudes from the cartridge holder, a bearing feature, e.g. a radially protruding section such as a flange, may be arranged. A distal surface of the bearing feature may abut a proximal surface of the cartridge holder, e.g. the proximal end face of the cartridge holder. In this way, a defined end position of the fixing member relative to the cartridge holder may be provided. Movement of the fixing member relative to the cartridge holder in the distal direction may be prevented by the bearing feature cooperating with the cartridge holder.

In an embodiment, by means of fixing members with fixing fingers of differing axial extensions, the fixing member can be adjusted to the length of the cartridge which is retained in the cartridge holder can be adjusted. Thus, the fixing member may be used to compensate for differences in cartridge dimensions which are to be retained in the cartridge holder. Specifically, fixing members having fixing fingers with different lengths may be applied for cartridges having different lengths. Consequently, one type of cartridge holder may be used and adjusted to cartridges of different dimensions using the fixing member. Different fixing members may differ only in the design of the fixing fingers, e.g. their length, and or in features arranged on an outer surface of the main body or fixing finger, e.g. connection or interface features discussed further below.

In an embodiment, the fixing member is axially rigid. That is to say, the fixing member is preferably not flexible or deformable when exposed to axially directed forces. As explained herein, one or more elements, particularly the fixing and/or securing finger(s) may be flexible, in particular elastically deformable. By an axially rigid fixing member, the cartridge can be very reliably secured in the cartridge holder.

In an embodiment, the cartridge holder is axially and/or radially rigid.

In an embodiment, the fixing member provides information about or is dedicated to or coded to the drug or medicament or drug formulation or medicament formulation contained in the cartridge and/or to the filling level of the cartridge. Accordingly, a standard cartridge holder can be used and the information about the drug or medicament contained in the cartridge can be provided by means of the fixing member. Two different drug or medicament formulations may have the same active pharmaceutical ingredient but different concentrations of this ingredient. Accordingly, by means of information provided by the fixing member, e.g. by the color or other visual and/or tactile indication provided on the fixing member, e.g. text, the user may verify that he intends to use the correct drug or medicament in the drug delivery device.

In an embodiment, the fixing member comprises one or more connection features which are configured to cooperate with corresponding connection features on a housing to secure the cartridge assembly to the housing, e.g. via a threaded or bayonet connection. The connection feature(s) may be arranged in the section of the fixing member which protrudes proximally from the cartridge holder, e.g. on a radially facing surface and/or outer surface of the fixing finger(s) or the main body.

In an embodiment, the cartridge assembly comprises one or a plurality of cartridge assembly interface features, which are configured to, preferably mechanically, cooperate with one or more corresponding housing interface features of a housing, expediently when attempting to connect the cartridge assembly to a housing to form a drug delivery device. The cartridge assembly interface feature may be provided on the fixing member. Cartridge assemblies containing different drugs or medicaments or different drug or medicament formulations may have different cartridge assembly interface features which are configured to be compatible only with housing interface features of a matching housing, i.e. a housing retaining a drive mechanism which is suitable to or designed to dispense the drug or medicament or the drug or medicament formulation contained in the cartridge. Accordingly, one of the cartridge assemblies, which is compatible with the housing, can be assembled to the housing and another, incompatible one cannot. Thus, by means of the cartridge interface feature(s) a mechanical coding may be provided. The cartridge assembly interface feature may be a coding feature. The cartridge interface feature(s) may be arranged in the section of the fixing member which protrudes proximally from the cartridge holder, e.g. on a radially facing surface and/or outer surface of the fixing finger(s) or the main body. If applicable, the interface feature and the connection feature may be formed by one feature or, alternatively, by different features.

Another aspect relates to a set of cartridge assemblies, where each cartridge assembly of the set is a cartridge assembly as described above and below. Two arbitrarily selected cartridge assemblies of the set, preferably any two cartridge assemblies which have different drugs or medicaments, different drug or medicament formulations and/or different filling levels in the cartridge of the cartridge assembly, differ in at least one of, an arbitrarily selected plurality of or all of the following characteristics:

The configuration of the cartridge assembly interface features of the two cartridge assemblies. The cartridge assembly interface features may be designed to be compatible only with housing interface features of different housings. For example, the cartridge assembly interface features of the different cartridge assemblies may be realized by protrusions having a defined angular width and/or radial extension where the interface features of the two cartridge assemblies have different widths and/or radial extensions where the width or radial extension of the interface features is unique in the set. Further a plurality of interface features may be provided on the respective assembly, where the interface features are a distributed, particularly circumferentially, in a pattern, where the patterns of the two cartridge assemblies are different, and the respective pattern is unique in the set. The interface feature may be formed by the fixing finger(s), for example, which may have a unique angular extension or pattern of angular extensions, for example.

The dimensions of the cartridges retained in the cartridge holder of the respective assembly. For example, one cartridge holder may retain a cartridge of one length or diameter and another cartridge assembly may retain a cartridge of a different length or diameter.

The color of the fixing members of the two different cartridge assemblies.

The configuration of the fixing fingers. For example, the axial extension or angular extension, e.g. the length of the fixing finger(s), may be different between the two cartridge assemblies.

Another aspect relates to a kit for assembling a cartridge assembly for a drug delivery device comprises a cartridge holder or a plurality of cartridge holders of the same dimensions or type and a plurality of fixing members which can be secured to the cartridge holder. The fixing members are designed to secure cartridges of different dimensions e.g. diameters and/or lengths within the cartridge holder. Thus, by choosing the appropriate fixing member, cartridges of different dimensions may be secured in the cartridge holder.

Another aspect relates to a method for manufacturing a cartridge assembly comprising the following steps:

Providing a cartridge holder. The cartridge holder which is provided may be a standard cartridge holder.

Providing a cartridge, which should be secured in the cartridge holder. The cartridge may be a cartridge of a dimension. However, different cartridges may have different dimensions as opposed to the standard cartridge holder which expediently only has one configuration. For example, a cartridge having different length and/or diameter may hold different volumes of drug or medicament formulation. For example, a cartridge of a volume of 3.0 ml and another cartridge of 1.5 ml may be used.

Determining the dimension of the cartridge. The determining of the dimension of the cartridge may include determining the length and/or diameter of the cartridge.

Thereafter, a particular fixing member may be chosen from a set of fixing members, which expediently comprises plurality of fixing members. Each fixing member of the set may be suitable to secure a cartridge of a specific dimension in the cartridge holder. Different fixing members of the set may be configured to secure cartridges of different dimensions in this cartridge holder. The particular fixing member which was chosen is particularly suitable to secure a cartridge of the dimension of the provided cartridge in the cartridge holder.

Thereafter, the particular or chosen fixing member may be fixed to the cartridge holder within the cartridge holder. The fixing member may be fixed to the cartridge holder before the cartridge is guided into the cartridge holder or afterwards. As detailed above, this may depend on the stiffness of the fixing fingers, for example.

Features disclosed above in conjunction with the cartridge assembly, the method, the kit, the set of cartridge assemblies and the drug delivery device should not be regarded as referring to only the recited aspect or embodiment. Rather, features also apply for other embodiments or aspects. Merely as an example, features disclosed in conjunction with the method do also apply for the cartridge assembly and vice versa. Of course, features disclosed in specific embodiments herein, can also be applied in combination with one another and/or with other features of other embodiments.

BRIEF DESCRIPTION OF THE FIGURES

Further features, advantages and advantageous embodiments of the present disclosure will become apparent from the following description of the exemplary embodiments in conjunction with the drawings.

Identical elements, identically acting elements, and elements of the same kind may be provided with the same reference numerals throughout the figures.

DETAILED DESCRIPTION

Figure 1:
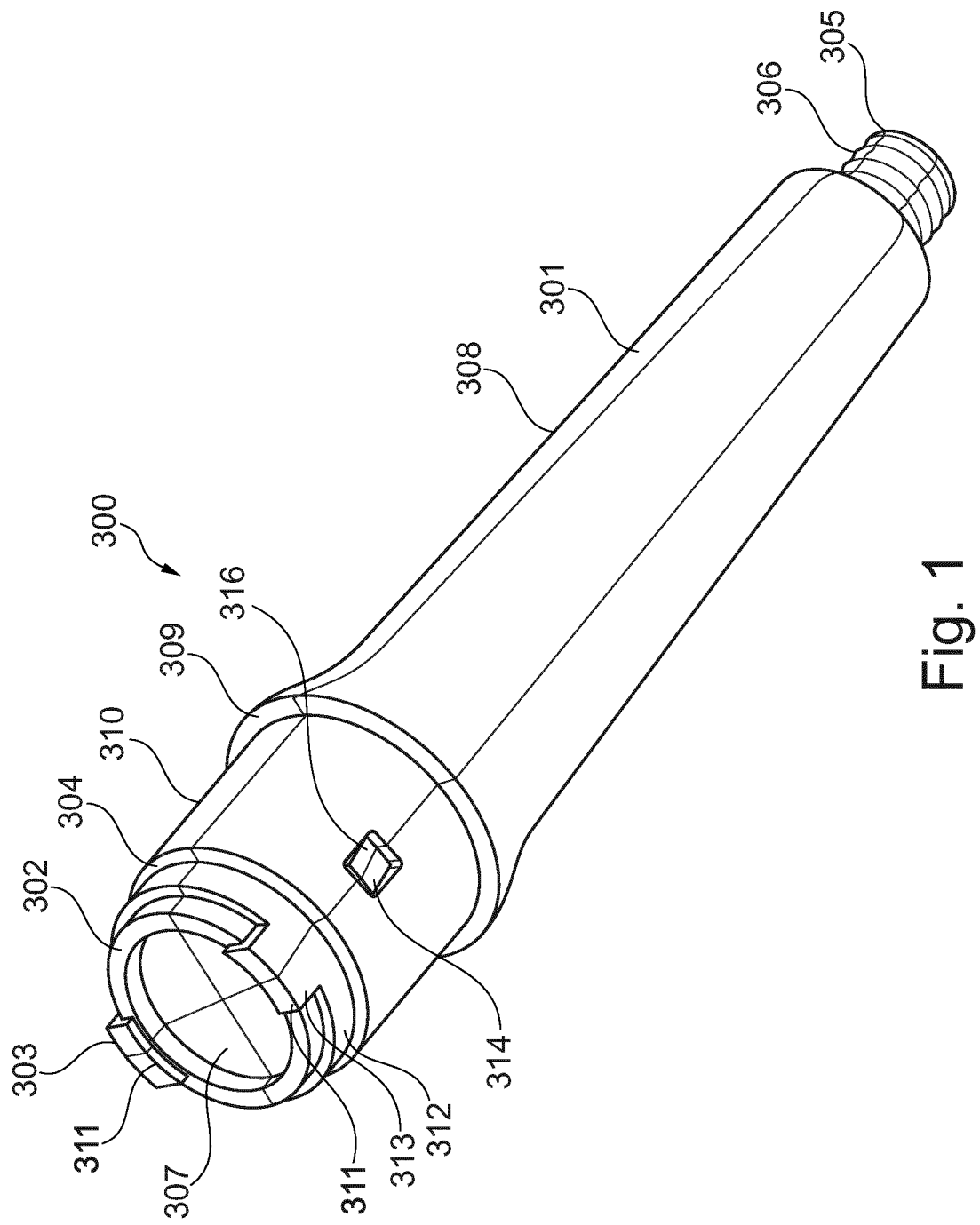
FIG. 1 shows on the basis of a schematic perspective view an embodiment of a cartridge assembly.

FIG. 1 shows a schematic perspective view of an embodiment of a cartridge assembly 300, in particular on the side of the proximal end. The cartridge assembly comprises a cartridge holder 301, a cartridge 302 and a fixing member 303. The cartridge holder 301 comprises a proximal end 304 and a distal end 305. At the proximal end, the cartridge holder has an opening through which the cartridge 302 may be introduced into the interior cartridge holding section of the cartridge holder 301. In the depicted embodiment that section is where the cartridge 302 is arranged in the holder. At the distal end 305 of the holder 301, a needle connector 306, e.g. a thread, may be provided. Via the connector, a needle unit (not illustrated) may be connected to the cartridge holder. For example, the needle hub of a standard needle unit may be threadedly engaged to the cartridge holder via the thread. When, the needle unit is mounted to the cartridge holder a needle of the unit may pierce a septum provided at the distal end of the cartridge 302, for example in a head portion of the cartridge which is connected to a tubular main body portion of the cartridge via a narrow neck portion. Via the needle of the needle unit, fluid communication may be provided between the interior of the cartridge and the exterior. If a bung 307, which closes the cartridge at its proximal end, is displaced relative to the cartridge in the distal direction, liquid drug or medicament contained in the cartridge 302 may be dispensed from the cartridge via the needle unit. The bung may be of rubber and/or be retained in the main body portion of the cartridge. The amount of drug or medicament in the cartridge is preferably sufficient for a plurality of doses, where the size of the dose may be set by the user or may be fixed, e.g. by the design of the drive mechanism used to deliver the drug or medicament from the drug delivery device which comprises the cartridge.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about-4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly (A21), Arg (B31), Arg (B32) human insulin (insulin glargine); Lys (B3), Glu (B29) human insulin (insulin glulisine); Lys (B28), Pro (B29) human insulin (insulin lispro); Asp (B28) human insulin (insulin aspart); human insulin, wherein proline in position B28 is replaced by Asp, Lys, Leu, Val or Ala and wherein in position B29 Lys may be replaced by Pro; Ala (B26) human insulin; Des (B28-B30) human insulin; Des (B27) human insulin and Des (B30) human insulin.

Examples of insulin derivatives are, for example, B29-N-myristoyl-des (B30) human insulin, Lys (B29) (N-tetradecanoyl)-des (B30) human insulin (insulin detemir, Levemir®); B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des (B30) human insulin, B29-N-omega-carboxypentadecanoyl-gamma-L-glutamyl-des (B30) human insulin (insulin degludec, Tresiba®); B29-N-(N-lithocholyl-gamma-glutamyl)-des (B30) human insulin; B29-N-(ω-carboxyheptadecanoyl)-des (B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

As depicted in FIG. 1, the cartridge 302 may protrude in the proximal direction from the cartridge holder 301. Preferably, when the cartridge is still full, where no drug or medicament has been dispensed yet from the cartridge, a section of the bung 307, preferably only a section, protrudes proximally from the cartridge holder. The majority of the cartridge 302 is preferably arranged in the holder, for example 90% or more of the total length of the cartridge. In this way, the cartridge may be protected adequately.

The cartridge holder 301 may, particularly between the proximal end 304 and a main body section 308, comprise a radially outwardly protruding step 309. The step 309 defines a proximally facing surface, which may be designed to abut a distal surface of a housing of a drug delivery device to which the cartridge assembly 300 may be connected in order to form a drug delivery device (see the housing 10 in FIG. 4, for example). A proximal section 310 of the cartridge holder, e.g. a section which is arranged proximally relative to the step 309, is expediently received in the housing. The main body section 308 of the cartridge holder may be arranged between the proximal section 310 and the needle connector 306.

Figure 2:
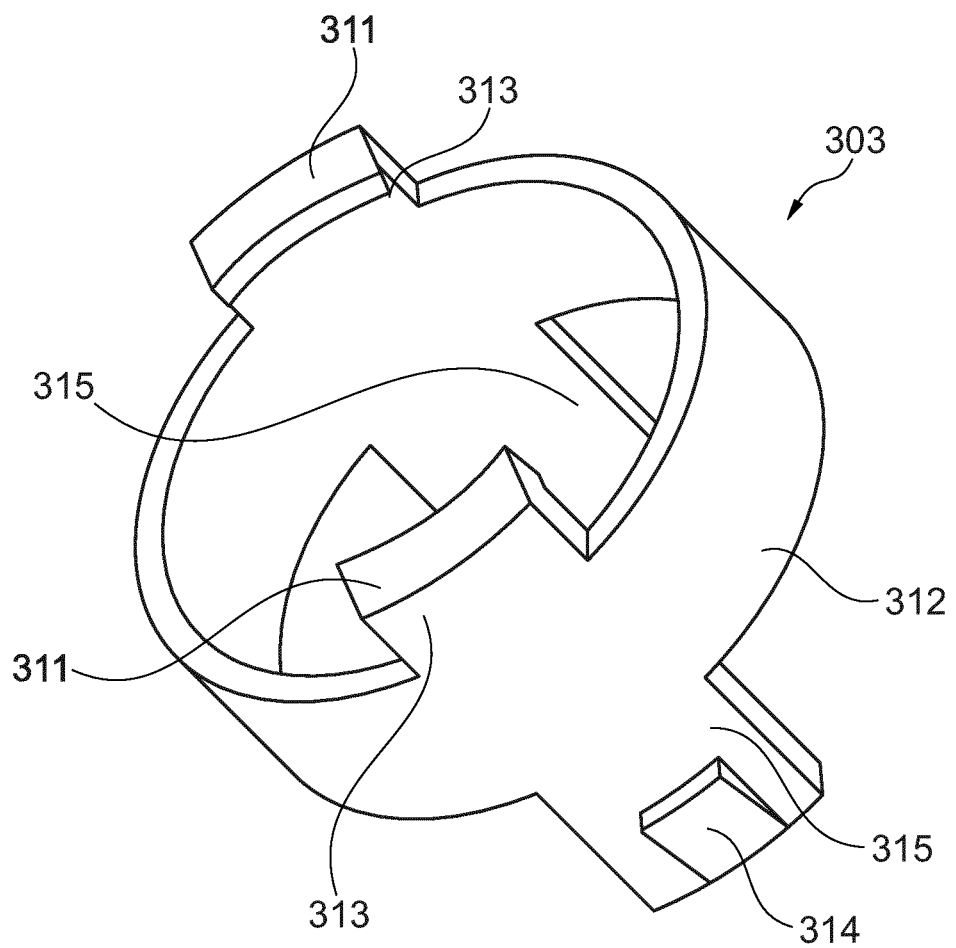
FIG. 2 shows an embodiment of the fixing member applied in the cartridge assembly of FIG. 1 on the basis of a schematic perspective view.

As depicted, the cartridge 302 is secured within the cartridge holder 301, preferably permanently and/or irreleasably, by the fixing member 303. FIG. 2 shows a schematic sectional view of the fixing member employed in the cartridge assembly of FIG. 1. The fixing member 303 comprises one or a plurality of fixing features 311. In the depicted embodiment, the fixing member 303 comprises two fixing features 311 which are oppositely disposed and face one another in the radial direction. The fixing features 311 extend in the radial inward direction. The fixing features are designed to abut (and in FIG. 1 do abut) a proximal end face of the cartridge 302. The distal face of the fixing feature abuts the proximal face of the cartridge. Preferably the fixing features do not extend radially over the proximal rim of the cartridge or only to a minor extent. Accordingly, distal movement of the bung by means of a drive mechanism of the drug delivery device, e.g. by a piston rod (not illustrated) which may travel through the opening defined by the fixing features 311, is not hindered by the fixing features 311. The fixing features 311 are connected to a main body 312 of the fixing member 303, which has the shape of a ring or sleeve, via fingers 313. The fingers extend in the axial direction, particularly in the proximal direction away from the main body 312. At a distance from the main body, the fixing features protrude in the radial direction from the fixing fingers 313.

The fixing member 303 further comprises one or a plurality of securing features 314. The securing features 314 may be provided to, preferably permanently, secure the fixing member 303 to the cartridge holder 301. The securing features 314 may be snap features. The securing features 314 are connected to the main body via securing fingers. The securing fingers extend in the axial direction away from the main body 312, preferably in the distal direction. The angular position of the securing fingers 314 may be aligned with the ones of the fixing fingers 313. The securing fingers 314 are expediently flexible. Particularly, they may be flexible in the radial direction, inwardly and/or outwardly. In this way, a radial movement which may be required for establishing a snap fit connection with the cartridge holder may be facilitated. A distal surface of the securing feature may be sloped so as to allow a radial deflection of the securing finger when the feature. A proximal surface may be less sloped and/or designed to prevent a proximal movement of the fixing member relative to the cartridge holder after it has been secured.

Figure 2A:
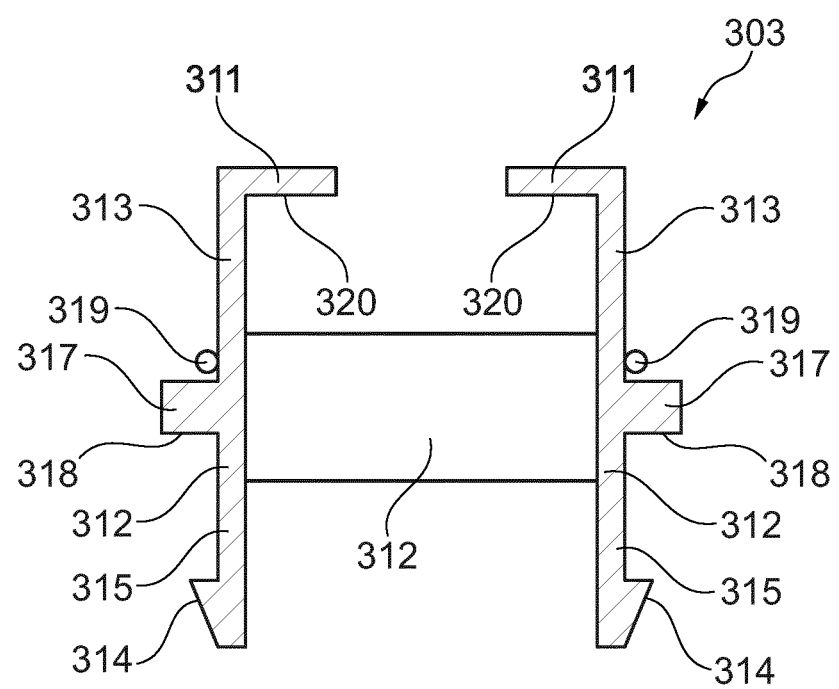
FIG. 2A shows an embodiment of the fixing member on the basis of a sectional view.

As depicted in FIG. 1, the fixing member is received in a region between the cartridge 302 and the cartridge holder 301 within the cartridge holder. In this way, particularly, the securing fingers and, if applicable a region, of the main body 312 (e.g., the entire main body or, as depicted only a part of the main body 312) may be received within the cartridge holder 301. A part of the main body 312 and/or the fixing features 311 may be arranged outside of the cartridge holder 301. In the part of the fixing member which protrudes from the cartridge holder, a bearing feature, e.g., a radially protruding feature such as a flange, may be arranged. In FIGS. 1 and 2 such a bearing feature 317 is not shown. However, it may be provided. In FIG. 2A an embodiment of a fixing member 303 having a bearing feature 317 is shown. Of course, also in the embodiment shown in FIGS. 1 and 2, an according bearing feature may be provided. The bearing feature 317 protrudes radially, particularly outwardly, from the main body 312. The bearing feature 317 may be embodied as a flange. Of course, other configurations also possible such as a plurality of circumferentially distributed bearing features or even a singular bearing feature which does not extend around the entire circumference. As the bearing feature 317 is provided in the region of the main body which is ring-like or sleeve-like, the bearing feature 317 is provided in a rigid and/or not easily radially and/or axially deformable section of the fixing member 303. The radial extension of the bearing feature 317, i.e. the distance by which it protrudes from the main body, is preferably chosen such that it does not radially protrude over the exterior surface of the cartridge holder when it is assembled to the cartridge holder. The bearing feature may end flush with the main body 308 of the cartridge holder in the radial direction. Alternatively or additionally, the radial extension of the bearing feature 317 is chosen such that the bearing feature radially protrudes with respect to the securing feature 314. Aside from the bearing feature 317 and another difference, which is disclosed further below, the fixing member 303 corresponds to the one previously described and which is also discussed in the following. Accordingly, the disclosure referring to FIGS. 1 and 2 also applies for FIG. 2A and vice versa. A distal surface 318 of the bearing feature 317 may be arranged to abut or abuts a proximal surface of the cartridge holder, e.g. the proximal end face of the cartridge holder. In this way, a defined end position of the fixing member relative to the cartridge holder may be provided. Movement of the fixing member relative to the cartridge holder in the distal direction may be prevented by the bearing feature cooperating with the cartridge holder. In FIG. 2A, the distal surface 320 of the fixing feature 311 which is arranged to abut the proximal end face of the cartridge is shown as well.

The securing features 314 of the fixing member 303 as shown in FIGS. 2 and 2A may engage with corresponding features 316 provided in the cartridge holder to secure the fixing member to the cartridge holder. In the depicted embodiment, this feature is a snap pocket 316. In FIG. 1, the pocket is depicted as being accessible from the outside. However, to avoid that the assembly can be easily disassembled, this access from the outside is expediently prevented. Accordingly, the snap pocket may be closed in the radial outward direction. However, if radial movement of the securing fingers in the inward direction is limited to an extent sufficient to prevent that the securing features are disengaged from the cartridge holder, which may be achieved by means of the outer wall of the cartridge abutting the securing fingers before the securing features disengage, then the corresponding feature in the cartridge holder may be accessible from the outside. The corresponding feature 316 may be provided in the proximal section 310 of the cartridge holder. Accordingly, when assembled to a housing to form a drug delivery device, the corresponding feature may be covered by the housing 10.

The cartridge assembly 300 as shown in FIG. 1 may form a single disposable item. Particularly, it may form an item of consumable material. Accordingly, the cartridge assembly 300 as depicted may be sold in a pharmacy to a user of a drug delivery device as a replacement item. As the cartridge is permanently secured in the holder, it cannot be easily disassembled or the fixing features may have to be destroyed to remove the cartridge from the cartridge holder. Accordingly, tampering with the cartridge assembly is readily visible to a user.

The fixing member 303 is designed to be usable or easily adjustable to cartridges having different dimensions, particular different lengths and/or diameters. In order to adjust to different lengths, the distance of the fixing features 311 from the main body 312 may be adjusted. For doing so, the fixing finger 313 may be provided with a greater or a smaller length. In order to adjust for a different diameter, the radial extension of the fixing features 311 may be adjusted, e.g. by providing them with a greater or smaller length. The fixing member may be formed unitarily. The fixing member may be a molded part, e.g. an injection molded part. The cartridge holder may be formed unitarily. The cartridge holder may be a molded part, e.g. an injection molded part.

The fixing features 311 may be connected to the main body 312 in a less resilient fashion or rigid than the securing features 314. In this way, it can be guaranteed that once the fixing member has been secured to the cartridge holder and the cartridge has been guided into the cartridge holder, the assembly is very stable and secure. If the fixing features are rigidly connected to the main body, e.g. by rigid fixing fingers, the cartridge may be introduced at first into the cartridge holder, when assembling the cartridge assembly, and, thereafter, the fixing member can be guided into the cartridge holder such that the securing fingers 315 extend between the cartridge and the cartridge holder, are resiliently deflected radially inwardly by means of the cartridge holder and deflect radially outwardly once the associated corresponding feature 316 has been reached on account of their resiliency. If the fixing features are resiliently connected to the main body, for example by resilient fixing fingers 313, the cartridge can be guided through the opening defined by the fixing features which may be maintained radially outwardly deflected until the cartridge has been reached its end position in the cartridge holder. Thus, in this case, the fixing member 303 can be connected to the cartridge holder 301 before the cartridge 302 is introduced. In each case, it is preferred that the fixing member is axially rigid, in particularly not flexible, when exposed to axial forces.

Before a cartridge is inserted into a cartridge holder to assemble a cartridge assembly, the dimension of the cartridge may be determined. For example, it may be determined which length or diameter the cartridge has. Depending on the result of the determination a suitable fixing member which is specifically designed to cooperate with a cartridge of that dimension is chosen from a set of fixing members. Accordingly, the fixing features of this fixing member are adapted to the cartridge of the particular dimension. Then, the cartridge assembly is assembled as described above. In this way, it can be ensured that a standard cartridge holder can be used together with different cartridges, where the adjustment to that cartridge dimension is achieved via the fixing member. Still further, fixing members used for different cartridges, either for cartridges of different dimensions and/or for cartridges containing different drugs or medicaments or formulations of drugs or medicaments or even filling levels, may be different. For example they may have different colors. Thus, information may be provided to the user about the content of the cartridge via the fixing member.

Different cartridge assemblies, particularly cartridge assemblies containing different drugs or medicaments or different drug or medicament formulations, may be uniquely coded. The coding or interface features may be provided on the fixing fingers 313 or that section of the main body which protrudes proximally from the cartridge holder 301. Alternatively or additionally, the coding or interface features may be formed by the fixing fingers, where different fixing members may have fixing fingers of different angular widths and/or angular positions on the main body 312. By means of the coding, it can be ensured that cartridge assemblies are only compatible with or can be mounted to housings housing drive mechanisms which are designed to dispense the particular drug or medicament or drug or medicament formulation contained in the cartridge assembly. The coding may be a mechanical coding and/or a color coding. For example, mechanical coding features may be provided on the fixing member which are uniquely matched to coding features provided in the housing of an associated drive mechanism. Accordingly, these coding features are configured to cooperate to permit an assembly of the cartridge assembly to the housing only if the coding features match. The coding may be achieved by means of cartridge assembly interface features and housing interface features which cooperate during connection of a cartridge assembly to a housing of a drug delivery device. Preferably, the cartridge assembly interface features are provided on the fixing member, e.g. on an outer surface of the main body 312 or the fixing fingers 313. They may be provided, for example by knobs. The interface features which are responsible for the coding may be the same or different from connection features which are required for the stable axial securing of the cartridge assembly to the housing. In FIGS. 1 and 2, such interface features are not shown. It is however readily apparent, that they could be provided. In FIG. 2A, cartridge assembly interface features and/or connection features 319 are shown. A plurality of features 319 may be provided. Expediently, the respective feature is provided in the region of the main body 312 such that the connection interface with the housing is provided in a mechanically stable region of the fixing member 303. The interface feature may be provided proximally offset from the bearing feature 317.

In a set of a plurality of cartridge assemblies, which are configured as previously described, two arbitrarily selected cartridge assemblies of the set may differ in the configuration of the cartridge assembly interface features of the two cartridge assemblies which are provided to cooperate with the housing interface features when attempting to connect or connecting the cartridge assembly to the housing. If the interface features of the housing and the cartridge assembly match, connection is allowed. If not, connection is denied. Additionally or alternatively, the dimensions, e.g. the length and/or diameter of the cartridges retained in the cartridge holder of the two cartridge assemblies may be different. Additionally or alternatively, the color of the fixing members may be different. Accordingly, the fixing member may be used to distinguish different cartridge assemblies from one another.

Figures 3, 4:
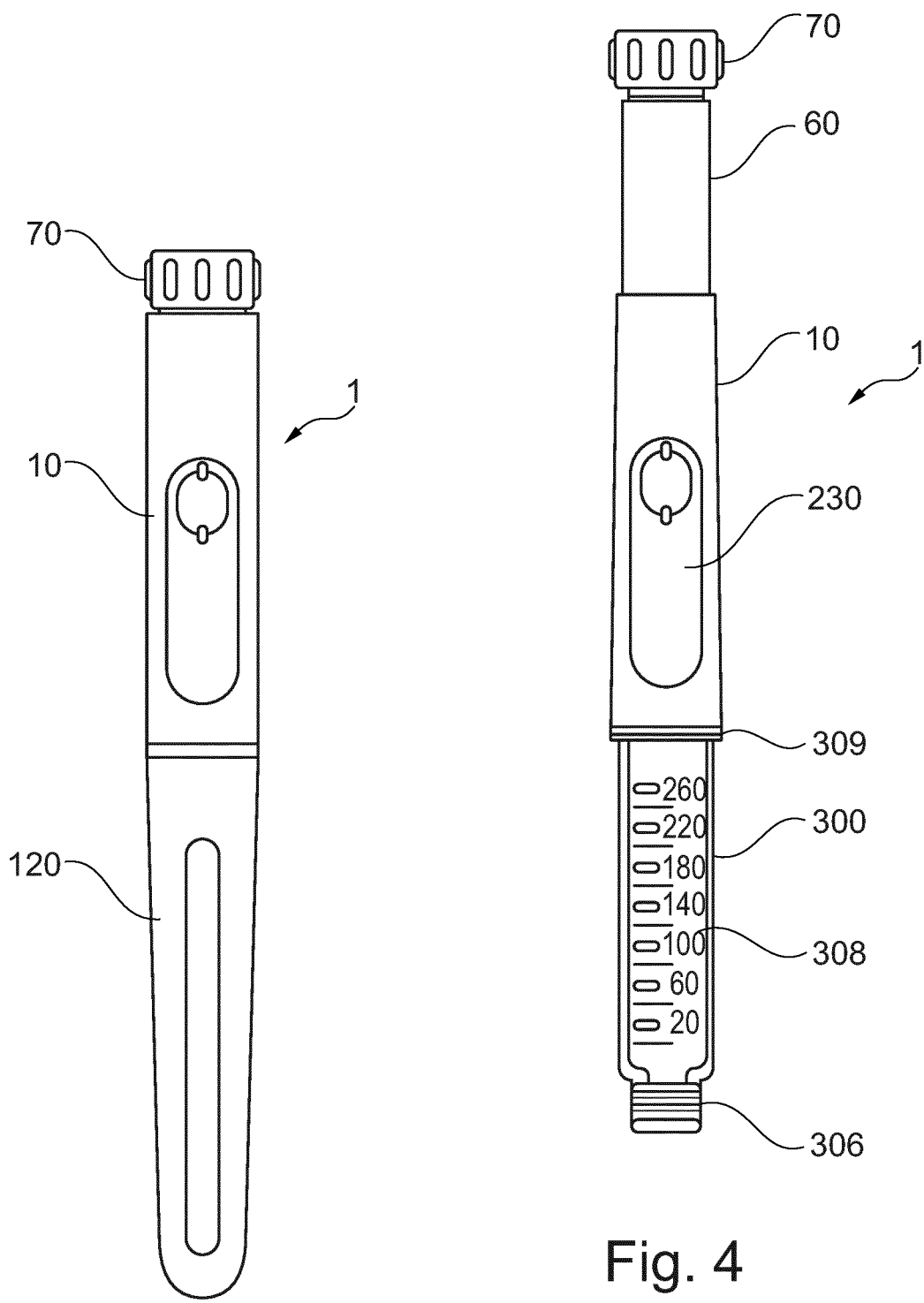
FIG. 3 illustrates an embodiment of a drug delivery device comprising the cartridge assembly in one state.
FIG. 4 illustrates the drug delivery device comprising the cartridge assembly in another state.

FIGS. 3 and 4 schematically illustrate embodiments of a drug delivery device suitable to be used in conjunction with the disclosed cartridge assembly. FIG. 3 shows the device 1 in a condition where a cap 120 is attached and covers the cartridge assembly 300. In FIG. 4 the cap has been removed. The cartridge assembly 300 is, expediently releasably, connected to a main body or housing 10 of the drug delivery device 1 as depicted in FIG. 4. The housing expediently defines the outer contour of the device and may be formed sleeve-like. A needle unit can be connected to the needle connector 306 in order to dispense drug from the device 1. A dose setting member 70 is movably retained in the housing 10 and can be manipulated by the user to set a dose. For example, it can be rotated relative to the housing to set a dose. The device may be a variable dose device, where the size of the dose is not predetermined by the design of the drive mechanism retained in the housing but rather may be changed by the user. In FIG. 4, a dose set condition of the drug delivery device is illustrated, where the numeral depicted in window 230 is changed as compared to FIG. 3 such that it illustrates the size of the currently set dose. The device may be designed such that during dose setting, the dose setting member 70 is displaced proximally relative to the housing 10. Alternatively, the dose setting member may stay the same axial position independently of the set dose. From the position depicted in FIG. 4, a dispensing action may be initiated, expediently by moving or exerting a force in the distal direction onto the dose setting member 70 or a dose dispensing member provided in a proximal end section of the drug delivery device 1. To dispense the dose, the bung is displaced distally relative to the cartridge, e.g. by a piston rod of the device (not explicitly shown).

The scope of protection is not limited to the examples given herein above. Any invention disclosed herein is embodied in each novel characteristic and each combination of characteristics, which particularly includes every combination of any features which are stated in the claims, even if this feature or this combination of features is not explicitly stated in the claims or in the examples.

REFERENCE NUMERALS 300 cartridge assembly
301 cartridge holder
302 cartridge
303 fixing member
304 proximal end
305 distal end
306 needle connector
307 bung
308 main body
309 step
310 proximal section
311 fixing feature
312 main body
313 fixing finger
314 securing feature
315 securing finger
316 corresponding feature
317 bearing feature
318 distal surface
319 interface feature
320 distal surface
1 drug delivery device
120 cap
70 dose setting member
10 housing
230 window

The invention claimed is:

1. A cartridge assembly for a drug delivery device, comprising:
    a cartridge holder comprising an interior cartridge holding section;
    a cartridge containing a drug, the cartridge being arranged in the interior cartridge holding section; and
    a fixing member axially secured to the cartridge holder to secure the cartridge irreleasably in the cartridge holder, wherein a portion of the fixing member is received in the cartridge holder, wherein the fixing member comprises one or more flexible securing fingers to secure the fixing member to the cartridge holder, the one or more flexible securing fingers being resiliently deflectable radially, and wherein the cartridge assembly is configured to be releasably secured to a housing of the drug delivery device.

2. The cartridge assembly of claim 1, wherein the cartridge assembly is one disposable item.

3. The cartridge assembly of claim 1, wherein the fixing member comprises a main body which extends circumferentially around the cartridge, wherein the main body is shaped as a ring or a sleeve.

4. The cartridge assembly of claim 1, wherein each securing finger comprises a securing feature to secure the fixing member axially with respect to the cartridge holder.

5. The cartridge assembly of claim 4, wherein the securing feature comprises a snap feature.

6. The cartridge assembly of claim 1, wherein the one or more flexible securing fingers extend away from the main body in an axial direction.

7. The cartridge assembly of claim 1, wherein at least a section of the fixing member is arranged between the cartridge and an inner wall of the cartridge holder.

8. The cartridge assembly of claim 1, wherein the fixing member comprises one or more fixing features arranged to retain the cartridge in the cartridge holder.

9. The cartridge assembly of claim 8, wherein a respective fixing feature of the one or more fixing features extends in a radial inward direction, wherein a distal surface of the respective fixing feature is arranged to contact a proximal end surface of the cartridge.

10. The cartridge assembly of claim 8, wherein the fixing member comprises one or more fixing fingers, wherein a respective fixing finger of the one or more fixing fingers comprises at least one of the one or more fixing features.

11. The cartridge assembly of claim 10, wherein each flexible securing finger comprises a securing feature to secure the fixing member axially with respect to the cartridge holder, and wherein the one or more fixing fingers are less flexible than the one or more flexible securing fingers.

12. The cartridge assembly of claim 8, wherein a bung is configured to close an interior of the cartridge at a proximal end of the cartridge, wherein the bung is movably retained in the cartridge, and wherein the one or more fixing features are proximally offset from a proximal end of the bung.

13. The cartridge assembly of claim 1, wherein a section of the fixing member and/or a section of the cartridge protrudes proximally from the cartridge holder.

14. The cartridge assembly of claim 1, wherein the fixing member comprises one or more cartridge assembly interface features configured to cooperate with housing interface features of the housing.

15. The cartridge assembly of claim 1, wherein the fixing member is irreleasably secured to the cartridge holder.

16. The cartridge assembly of claim 1, wherein the fixing member is axially and rotationally secured to the cartridge holder, wherein relative rotational movement between the fixing member and the cartridge holder is prevented in two opposite rotational directions.

17. The cartridge assembly of claim 1, wherein the drug delivery device is an injection device.

18. A drug delivery device, comprising:
    a housing;
    a cartridge holder comprising an interior cartridge holding section, wherein the cartridge holder is releasably secured to the housing;
    a cartridge containing a drug, the cartridge being arranged in the interior cartridge holding section; and
    a fixing member axially secured to the cartridge holder to secure the cartridge irreleasably in the cartridge holder, wherein a portion of the fixing member is received in the cartridge holder, wherein the fixing member comprises one or more flexible securing fingers to secure the fixing member to the cartridge holder, the one or more flexible securing fingers being resiliently deflectable radially.

19. The drug delivery device of claim 18, wherein the drug contained in the cartridge is a medicament.

20. A method of using a drug delivery device comprising a cartridge assembly to dispense a drug from a cartridge of the cartridge assembly, comprising:
    providing the cartridge assembly with a cartridge holder comprising an interior cartridge holding section for receiving the cartridge containing the drug, the cartridge assembly further including a fixing member axially secured to the cartridge holder to secure the cartridge irreleasably in the cartridge holder, wherein a portion of the fixing member is received in the cartridge holder, wherein the fixing member comprises one or more flexible securing fingers to secure the fixing member to the cartridge holder, the one or more flexible securing fingers being resiliently deflectable radially;
    releasably securing the cartridge assembly to a housing of the drug delivery device; and
    dispensing the drug from the cartridge of the cartridge assembly.

* * * * *